United States Patent [19]

Spiro

[11] Patent Number: 4,771,005

[45] Date of Patent: Sep. 13, 1988

[54] REAGENTS, TEST KITS AND METHODS FOR THE DETECTION OF CANNABINOIDS

[75] Inventor: Baruch Spiro, Jerusalem, Israel

[73] Assignee: Erez Forensic Technology Ltd., Israel

[21] Appl. No.: 619,901

[22] Filed: Jun. 12, 1984

[30] Foreign Application Priority Data

Jun. 27, 1983 [IL] Israel .......................................... 69075
Jul. 25, 1983 [IL] Israel .......................................... 69316

[51] Int. Cl.$^4$ ...................... G01N 21/78; G01N 33/94
[52] U.S. Cl. .......................................... 436/93; 422/61;
436/131; 436/164; 436/901; 436/903; 534/558;
534/560; 534/561; 534/563
[58] Field of Search ...................... 422/61; 436/93, 127,
436/131, 164, 166, 901, 903; 534/558, 559, 560,
561, 563, 564

[56] References Cited

U.S. PATENT DOCUMENTS

| | | | |
|---|---|---|---|
| 2,101,664 | 12/1937 | Wyler | 534/558 X |
| 2,498,722 | 2/1950 | Straley | 534/560 X |
| 2,861,065 | 11/1958 | Herrick | 534/558 X |
| 2,864,816 | 12/1958 | Nicolaus et al. | 534/559 X |
| 3,676,072 | 7/1972 | Krivis | 422/61 X |
| 3,748,098 | 7/1973 | Dutch | 422/61 |
| 3,850,576 | 11/1974 | Rittersdorf et al. | 436/903 X |
| 3,880,588 | 4/1975 | Rittersdorf et al. | 436/903 X |
| 3,930,856 | 1/1976 | de Moira et al. | 534/558 X |
| 3,955,926 | 5/1976 | Fischer | 422/56 X |
| 3,957,489 | 5/1976 | Moore | 534/560 X |
| 4,132,553 | 1/1979 | Burkle et al. | 534/561 X |
| 4,196,167 | 4/1980 | Olsen | 422/61 |
| 4,288,344 | 9/1981 | Reiss | 436/901 X |
| 4,468,467 | 8/1984 | Babb et al. | 436/903 X |
| 4,525,582 | 6/1985 | Amato et al. | 534/560 X |
| 4,533,620 | 8/1985 | Walls et al. | 534/558 X |

FOREIGN PATENT DOCUMENTS

0681355 8/1979 U.S.S.R. .............................. 436/903

OTHER PUBLICATIONS

Ikari et al., Chemical Abstracts, vol. 86, Abstract No. 86:180697q, 1976.
De Faubert Maunder, Bulletin on Narcotics, vol. 26, No. 4, pp. 19–26, 1974.
De Faubert Maunder, J.A.P.A., vol. 7, pp. 24–30, 1969.
Thornton et al., J. Forens. Sci. Soc., vol. 12, pp. 461–505, 1972.
De Faubert Maunder, J. of Chromatography, vol. 100, pp. 196–199, 1974.
Lau-Cam et al., J. of Pharmaceutical Sciences, vol. 68, No. 8, pp. 976–978, 1979.
"Isolation and Identification of Drugs", Edited by Clarke, Published by Pharmaceutical Press (London), pp. 235–236, 797 and 802, 1969.
De Faubert Maunder, J. Pharm. Pharmac., vol. 21, pp. 334–335, 1969.

Primary Examiner—Barry S. Richman
Assistant Examiner—Robert J. Hill, Jr.

[57] ABSTRACT

The invention provides a stable solid reagent for use in a prepackaged test kit for the detection of cannabinoids comprising a diazonium salt which undergoes characteristic color change when combined with a cannabinoid under basic conditions, the salt comprising an anion capable of causing the entire salt including the diazonium cation thereof to dissolve in an organic solvent when combined therewith to form a stable liquid reagent for the detection of cannabinoids. The invention also provides a stable liquid reagent comprising the aforementioned diazonium salt and an organic solvent as well as providing prepackaged reagent test kits containing the aforementioned reagents and methods for detecting cannabinoids using the reagents of the invention.

18 Claims, No Drawings

REAGENTS, TEST KITS AND METHODS FOR THE DETECTION OF CANNABINOIDS

The present invention relates to a test kit and method for the detection of cannabinoids.

More particularly, the present invention relates to a prepackaged test kit containing a substantially stable cannabinoid detection reagent for the detection of marihuana, hashish and liquid cannabis.

Cannabis derivatives (marihuana, hashish and liquid cannabis) will continue to be the primary drugs of abuse throughout the world.

The pharmacological effects usually associated with marihuana are produced by $(-)-\Delta^8$-trans-tetrahydrocannabinol and $(-)-\Delta^9$-trans-tetrahydrocannabinol (THC) as reported by Bicher, H. I. and R. Mechoulam: Arch.Int. Pharmacodyn.Ther., 172, p.26 (1968). The other main cannabinoids present are cannabidiol (CBD) and Cannabinol (CBN), the precursor and degradation products of $\Delta^9$-THC respectively.

Because of its widespread illicit use, marihuana (Cannabis Sativa) has become the focus of numerous analytical methods of investigation with marihuana and hashish traditionally having been identified in the past by a combination of chemical tests of the cannabinols (Beam and Duquenois) and botanical examination.

Since Cannabinoids are phenolic compounds, they couple with diazonium salts to produce a characterizing color, under mildly basic conditions. The chromatograms used for TLC technique are therefore exposed to ammonia vapor or, to form more stable colors, they are sprayed with 10% sodium carbonate of 0.1N NaOH solutions after application of the diazonium salt.

The well known Beam test is performed either with alkaline (2% ethanolic KOH) or acidic (95% ethanol saturated with HCl) reagents, however many known samples of Cannabis fail to yield a positive reaction with either reagent, and the test has in recent years been shown to be specific for cannabidiol, while yielding no reaction with THC. Consequently, it is no longer employed by most forensic laboratories, although it was once widely used.

The Duquenois Levine test is now the most widely used color test for Cannabis. It is specific for phenols containing a long alkyl side chain. Levine's modification of the test provides an extraction of the color from the vanillin-acetaldehyde-THC complex into chloroform. A positive test is obtained only if the color formed is extracted into the organic phase.

This modification renders the test specific for THC, since many of the colored complexes formed with the reagent are not chloroform soluble.

Although a number of substances give colors with the Duquenois reagent, the colors obtained are different from the normal color obtained with marihuana so that an experienced analyst would not be confused by them.

Thornton, J. I. and Nakamura, G. R., "The Identification of Marihuana", Journal of Forensic Science Society, vol. 12, 1972, pp. 461–505 and Goddard, K., 37th Semiannual Seminar, California Association of Criminalists, Newport Beach, Calif., 1971, report however, that olivetol, mace, nutmeg, currants, terpens and phenolics all give colors with the Duquenois-Levine test which could be confused with the colors for marihuana and hashish. The colors formed with the phenolic substances develop immediately upon the addition of the concentrated hydrochloric acid. The reaction with marihuana, however, is relatively slow and there is a succession of color changes befoe the final purple color develops.

While testing marihuana with the modified Duquenois test, it will be found that the color in the chloroform layer is stable and it will not change appreciably even when kept overnight. With most of the other substances, if there is a pink color extractable into the chloroform layer, it will often be found that the color is not stable and that it will either fade or change its color over as short a time as an hour.

Some compounds can be distinguished from marihuana merely by repeating the Duquenois test and using a very small amount of sample. Then it may be found that there will now be no extraction of color into the chloroform layer, while conversely in some cases, the addition of the chloroform will even decolorize the aqueous layer if the exhibit is marihuana.

Since the active ingredient of cannabinoids is THC which has been synthesized (and thus a reference standard is available) identification may be accomplished using chromatographic techniques such as thin layer chromatography (TLC). TLC technique has found extensive application in the qualitative study of marihuana. The products, usually in the form of leaves, stems or seeds, necessitate an initial extraction, filtration, evaporation to dryness and subsequent chromatographic identification using a number of solvent systems.

Detection of cannabinoids is accomplished by freshly prepared solution of Fast Blue BB salt (4-Benzamido-2,5-diethoxyphenyl diazonium chloride) in cold 0.1N NaOH. The latter detection method provides great sensitivity (detectable level 50 ng for THC and CBD) and a distinct color differentiation for the major components: CBD, orange; THC, scarlet; CBN, violet. There is no compound or mixture of compounds reported that will coincidentally chromatograph and develop the same colors as found in marihuana and hashish samples.

As will be realized, on numerous occasions a police officer has to determine whether or not a suspected material is marihuana and thus quickly establish probable cause.

Often, the laboratory is closed, or many miles away, and he has no way of making this determination. A test kit can help an officer detect the presence of the marihuana.

It is well known that chemical spot tests contribute and are used for identification of various substances. Chemical spot test kits have been commercially developed and are used by many law enforcement agencies for the identification of narcotics and drugs of abuse. Most of the commercial kits contain reagents only for the Duquenois-Levine test. The sensitivity level for this reagent is 3 mg.

Some of the commercial kits also contain the Fast Blue BB salt reagent in the solid state. The reagent is dissolved just before use. This dye normally responds strongly and instantaneously to all cannabis samples. This reagent has a practical advantage as a field test reagent, for all samples of different age or origin yield the same hue.

Thus, as reported by Maunder, M. J., "A Simple and Specific Test for Cannabis", Journal of the Association of Public Analysts, Vol. 7, March 1969, pp. 24–30, of 236 herbal materials tested, only 2 gave a color that might be confused with Cannabis. Both of these substances were tested with a modified Duquenois-Levine test and were negative.

It has thus been determined that in the hands of an experienced analyst, a diazonium dyestuff is capable of detecting traces of cannabis (such as its resin) adhering to the skin or any other contaminated surface. Solvent washing of a suspect's finger with petroleum spirit onto a filter paper yields sufficient cannabinoidol material to yield a positive response. The skin of persons handling large quantities of cannabis, such as habitual smokers or smugglers, absorbs cannabinoids. These are not readily removed by simple wiping or even by soap and water washing and can be detected one day later with ease and up to two days in the case of unwashed skin.

There are however problems with said diazonium salts with regard to their instability, since once formed, aromatic diazonium salts react with a host of different nucleophile. The Fast Blue BB Salt is attacked by the weakly nucleophile-$H_2O$ and is decomposed to the corresponding phenol. In slightly basic solution, necessary for cannabis detection, this process is accelerated. With a life span of only days before decomposing, prepackaged solutions of diazonium salts have not been commercialized, despite the proven superiority of such salts and the widespread demand thereof.

In recent years many attempts have been made to stabilize diazonium salts, so that they could be used in detection kits.

One proposal was to use a solid diluent such as anhydrous sodium sulphate to form a solid reagent. The solid diluent added to the dyestuff serves three main purposes. Firstly, it dilutes the highly reactive dye and effectively prevents the addition of too large a quantity. Secondly, it protects the dye from moist atmosphere. Thirdly, it acts as a mild light screen. Anhydrous sodium sulphate functions in all three capacities - inert diluent, desiccant and light screen.

However, during the storage in excess of 3 months at ambient temperatures, some batches of anhydrous sodium sulphate were found to be unsatisfactory. Excessive amounts of residual moisture or alkalinity were identified as causes of premature decomposition. Mixtures of dry salt with an inert material, to be dissolved just before use were also found to be too cumbersome as reported by De Faubert Maunder, M. J., Bulletin on Narcotics, vol. XXVI, No. 4, pp. 19–26 (Oct. Dec.1974).

A second proposal was to prepare sensitised paper (Merck Ltd. Catalog No. 9500). In said product the sensitised papers of the dyestuff are presented as a pad at the end of a plastic handle. In operation, the test is both sensitive and simple. A major disadvantage of this alternative approach is the risk of contamination. Long term storage is not possible. These papers are not stable in moist atmosphere.

A third approach was to prepare aqueous solutions of diazonium salts, however, it was found that such aqueous solutions are not stable for extended periods essential for kit reagent use.

De Faubert Maunder, J. J., J. Phar. Pharmacol. 1969, 21, 334 reports that addition of methanol improves stability in excess of one hour. Addition of dilute hydrochloric acid to this extended stability to several days. Storage beyond a week however was difficult, rendering the reagent unsuitable for use in field test kits.

Recently, in U.S. Pat. No. 4,288,344, there is described and claimed a stable diazonium salt generator for improved marihuana analysis based on a solution of Zirconium Oxychloride, Sodium Cobaltinitrite and Fast Blue BB Salt. This mixture dissolved in Methyl Cellosolve, forms a characteristic red dye with marihuana phenols when developed by an equal volume of aqueous alkaline solution. The reagents remain effective over six months.

It is interesting to note that said Patent in summarizing the invention in Col. 1, lines 39–43, states that "instead of attempting to keep Diazonium Salt solutions stable, proven unsuccessful in over 50 years of attempts, this invention introduces a unique diazotizing composition, able to diazotize precursor Amines to their corresponding Diazonium Salts "in situ".

The proposed reagent of said Patent also suffers however from three major disadvantages:
(1) A life span of only 6 months is not enough for a commercial test kit.
(2) Methyl Cellosolve is highly poisonous.
(3) This mixture cannot be prepackaged in an aerosol sprayer. By adding Freon 12 the salts will precipitate.

In contradistinction to the approaches previously taken and overcoming all of the disadvantages of the prior art products, after much research and development it has now been surprisingly discovered that, contrary to the above-quoted statement in said prior art Patent, it is indeed possible to produce stable solutions of diazonium salts for use in cannabinoid detection test kits and having a stability of well over a year.

Thus the present invention provides a stable liquid reagent for use in a prepackaged test kit for the detection of cannabinoids comprising an organic solvent and a diazonium salt which undergoes characteristic color change when combined with a cannabinoid under basic conditions, said salt comprising an anion capable of causing the entire salt including the diazonium cation thereof to dissolve in said organic solvent.

The present invention also provides a stable solid reagent for use in a prepackaged test kit for the detection of cannabinoids comprising a diazonium salt which undergoes characteristic color change when combined with a cannabinoid under basic conditions, said salt comprising an anion capable of causing the entire salt including the diazonium cation thereof to dissolve in an organic solvent when combined therewith to form a stable water-free liquid reagent for the detection of cannabinoids.

In another aspect of the invention there is provided a method for detecting cannabinoids comprising
(a) providing a stable water-free liquid reagent containing an organic solvent and a diazonium salt which undergoes characteristic color change when combined with a cannabinoid under basic conditions, said salt comprising an anion capable of causing the entire salt including the diazonium cation thereof to dissolve in said organic solvent;
(b) contacting said reagent with a suspected cannabinoid containing sample; and
(c) developing a characteristic identifying color by addition of a basic solution.

Preferably said diazonium cation is selected from the group consisting of 4-benzamido-2,5-diethoxyphenyl diazonium cation, (Fast Blue BB diazonium cation - color index 37175), 4,4'-diazonium cation-3,3'dimethoxy biphenyl (Fast Blue B diazonium cation - color index 37235), 1-diazonium cation-2-methoxy-4-nitrobenzene (Fast Red B diazonium cation - color index 37125), 4-diazonium cation - 2',3-dimethylazobenzene (Fast Garnet GBO - color index 37210) and 2- diazonium cation 4',5-dimethyl-2'-nitro-3-methoxyazobenzene (Fast Cornith V - color index 37220)

Said anion can preferably be an inorganic anion such as perchlorate or thiocyanate, an arylsulfonate such as trinitrobenzenesulfonate, anthracene-2-sulfonate, a phenoxide such as picrate or 2,4-dinitronaphthoxide, a carboxylate such as salicylate or phenoxymethylpenicillinate or a barbiturate such as amobarbiturate or hexobarbiturate and the picrate and perchlorate anion are especially preferred, having a shelf-life at room temperature of over a year and a shelf-life of several years under refrigeration conditions.

Said organic solvent is preferably selected from the group consisting of dichloromethane, chloroform, methanol, tetrahydrofuran, acetone and nitrobenzene.

It will be recognized however that any suitable cannabinoid detecting diazonium cation, any anion of a diazonium salt, capable of causing the entire salt including the diazonium cation thereof to dissolve in an organic solvent, and any suitable organic solvent can be used in accordance with the present invention and are included within the scope thereof.

The invention further provides a prepackaged stable two-liquid reagent test kit for the detection of cannabinoids comprising:
  (a) a substantially stable water-free liquid reagent containing an organic solvent and a diazonium salt which undergoes characteristic color change when combined with a cannabinoid under basic conditions, said salt comprising an anion capable of causing the entire salt including the diazonium cation thereof to dissolve in said organic solvent, and
  (b) a color developing basic solution.

While aqueous basic developing solutions can theoretically be used in conjunction with the novel reagent of the present invention preferably said basic solution comprises an organic base since such a base can be put in an aerosol spray which uses an organic propellant. Said organic base is preferably selected from the group consisting of triethanolamine, 4-dimethylaminopyridine, 2-dimethylaminopyridine, 2,4,6-trimethylpyridine, piperidine, and 4-(2-piperidinoethyl) pyridine and provided in a solvent selected from a group consisting of dichloromethane, chloroform, acetone, ethanol, methanol and ethylacetate.

Both said stable liquid reagent and said color developing base can be packaged in preferred embodiments of the present invention in separate aerosol containers and dispensers in combination with a propellant selected from compressed air, a fluorohydrocarbon, a chloro-fluorohydrocarbon, $CO_2$ gas, nitrous oxide or $N_2$ gas, although simple pump (without propellant) dispensers can also be used.

The concentration of the diazonium salt in the organic solvent can range from about 0.1% by weight/volume up to 1% and it is preferred that sufficient salt be present in the solution so that one spray application will dispense sufficient salt to bring out the characteristic color reaction with cannabinoids.

As stated, the solution will preferably be contained under pressure with a propellant and any of the standard propellants may be used.

A preferred field test kit contains:
  (a) Diazonium salt in organic solvent (preferably in a pressurized aerosol container),
  (b) Basic compound in organic solvent (preferably in a pressurized aerosol container) and
  (c) Filter paper.

While the invention will now be described in connection with certain preferred embodiments in the following examples it will be understood that it is not intended to limit the invention to these particular embodiments. On the contrary, it is intended to cover all alternatives, modifications and equivalents as may be included within the scope of the invention as defined by the appended claims. Thus, the following examples which include preferred embodiments will serve to illustrate the practice of this invention, it being understood that the particulars shown are by way of example and for purposes of illustrative discussion of preferred embodiments of the present invention only and are presented in the cause of providing what is believed to be the most useful and readily understood description of formulation procedures as well as of the principles and conceptual aspects of the invention.

EXAMPLE 1

A. 4-benzamido-2,5-diethoxyphenyl diazonium chloride (2.4 m mole) is dissolved in water (30 ml) at 0° C. picric acid (2.4 m mole) in little water is added all at once. The precipitate formed is filtered by suction and dried over $P_2O_5$ (phosphorous pentoxide) under vacuum to give a yellow solid [1.2 gr; 95% yield]. The yellow solid [4-diazonium picrate-2,5-diethoxybenzanilide], is dissolved (0.5/w/v) in dichloromethane. This is stock solution A[diazotizing reagent]. B. Triethanolamine is dissolved in (1%,w/v) ethanol. This is stock solution B (developer reagent).

EXAMPLE 2

A. Stock solutions A and B prepared according to Example 1 are placed in separate aerosol containers.

B. A suspected material is dissolved in small amount of chloroform and spot placed for development on a silica or alumina TLC plate in a TLC chamber containing a shallow layer of developing solvent (chloroform: pet.ether - 85:15). The plate is then removed and dried.

C. The cannabinoids are detected by spraying the two solutions successively. The order has no meaning. The following colors are immediately developed: CBD- orange, THC- scarlet, CBN - violet. Using phase transfer techniques additional stable diazonium salts were prepared.

EXAMPLE 3

Fast Blue BB Salt (chloride salt - ½ $ZnCl_2$) (2.4 m mole) in water (100 ml) at 0° C. was added to dichloromethane (100 ml) and picric acid (2.4 m mole). The mixture was vigorously agitated at 0° C. The diazonium ion transferred to the organic layer. The organic solvent was removed to give a yellow solid (1.23 gr, 95% yield).

EXAMPLE 4

A mixture of Fast Blue BB Salt (chloride salt, ½ $ZnCl_2$) (2.4 m mole) and sodium perchlorate (2.4 m mole) in water and dichloromethane was agitated vigorously at 0° C. The organic solvent was removed to give a yellow solid (0.88 gr; 90%).

EXAMPLE 5

The procedure described in Example 3 was repeated except that the picric acid was replaced by trinitrobenzenesulfonic acid (2.4 m mole) (1.41 gr; 92%).

EXAMPLE 6

The procedure described in Example 4 was repeated, except that the sodium perchlorate was replaced by potassium thiocyanate (2.4 m mole) (0.8 gr; 90%).

EXAMPLE 7

Fast Blue BB Salt (chloride salt ½ ZnCl$_2$) (2.4 m mole) in water (100 ml) at 0° C. was added to picric acid (2.4 m mole) in 100 ml of water. The solution was filtered by suction. The solid was dried over P$_2$O$_5$ (1.16 gr; 90% yield).

EXAMPLE 8

A. A field test kit for preliminary screening of suspected material to be followed later by court admissable TLC tests was prepared by providing stock solution A and stock solution B from Example 1 in two separate medicine bottles equipped with droppers.

B. A few miligrams of suspected material were placed on white paper cloth or spot plate, then successively covered by one drop of each solution. When the suspected material is marihuana or hashish, there is produced a red dye color.

EXAMPLE 9

4-Benzamido-2,5-diethoxyphenyl diazonium chloride (2-4 m mole) is dissolved in water (30 ml) at 0° C. Picric acid (2.4 m mole) in little water is added all at once. The precipitate formed is filtered by suction and dried over P$_2$O$_5$ (phosphorous pentoxide) under vacuum to give a yellow solid [1.2 gr; 95% yield]. The yellow solid [4-diazonium picrate-2,5-diethoxybenzanilide] can be packaged and sold for later combination with a suitable organic solvent such as dichloromethane.

EXAMPLE 10

4,4'-Diazonium chloride-3,3'-dimethoxy biphenyl (2.4 m mole) is dissolved in water (30 ml) at 0° C. Picric acid (4.8 m mole) in little water is added all at once. The precipitate formed is filtered by suction and dried over P$_2$O$_5$ (phosphorous pentoxide) under vacuum to give a yellow solid [1.3 gr; 80% yield].

Name of product is: 4,4'-Diazonium picrate-3,3-dimethoxy biphenyl.

EXAMPLE 11

The procedure described in Example 10 was repeated except that the picric acid was replaced by sodium perchlorate (2.4 m mole) (0.84 gr; 70% yield).

Name of product is: 4,4'-Diazonium perchlorate-3,3'-dimethoxy biphenyl.

It will be evident to those skilled in the art that the invention is not limited to the details of the foregoing illustrative embodiments and examples and that the present invention may be embodied in other specific forms without departing from the essential attributes thereof, and it is, therefore, desired that the present embodiments and examples be condidered in all respects as illustrative and not restrictive, reference being made to the appended claims, rather than to the foregoing description, and all changes which come with the meaning and range of equivalency of the claims are, therefore, intended to be embraced therein.

What is claimed is:

1. A method of detecting cannabinoids comprising applying a stable water-free liquid reagent to a sample suspected of containing cannabinoids and then applying a developing liquid to the sample to produce a color change in the sample when the sample contains cannabinoids, wherein said stable water-free liquid reagent comprises an organic solvent and a diazonium salt which undergoes a characteristic color change when combined with cannabinoids under basic conditions, wherein said salt comprises a diazonium cation and an anion capable of causing the entire salt, including the diazonium cation thereof, to dissolve in the organic solvent, and wherein said developing liquid comprises a color-developing basic liquid capable of developing a color in the presence of the water-free liquid reagent and cannabinoids.

2. A method of detecting cannabinoids comprising applying a water-free liquid reagent to a sample suspected of containing cannabinoids and then applying a developing liquid to the sample to produce a color change in the sample when the sample contains cannabinoids, wherein said water-free liquid reagent comprises an organic solvent and a diazonium salt which undergoes a characteristic color change when combined with cannabinoids under basic conditions, wherein said salt comprises a diazonium cation and an anion selected from the group consisting of perchlorate, thiocynate, trinitrobenzenesulfonate, anthracene-2-sulfonate, picrate, 2,4'-dinitro-α-napthoxide, salicylate, phenoxymethyl-penicillinate, amobarbiturate, and hexobarbiturate anions, which anion causes the entire salt, including the diazonium cation thereof, to dissolve in the organic solvent, and wherein said developing liquid comprises a color-developing basic liquid capable of developing a color in the presence of the water-free liquid reagent and cannabinoids.

3. A method of detecting cannabinoids comprising applying a water-free liquid reagent to a sample suspected of containing cannabinoids and then applying a developing liquid to the sample to produce a color change in the sample when the sample contains cannabinoids, wherein said water-free liquid reagent comprises an organic solvent and a diazonium salt which undergoes a characteristic color change when combined with cannabinoids under basic conditions, wherein said salt comprises a diazonium cation and an anion selected from the group consisting of picrate and perchlorate anions, which anion causes the entire salt, including the diazonium cation thereof, to dissolve in the organic solvent, and wherein said developing liquid comprises a color-developing basic liquid capable of developing a color in the presence of the water-free liquid reagent and cannabinoids.

4. The method according to claim 3 wherein said diazonium cation is selected from the group consisting of 4-benzamido-2,5-diethoxyphenyl diazonium cation, 4,4'-diazonium cation-3,3'-dimethoxy biphenyl, 1-diazonium cation-2-methoxy--4-nitrobenzene, 4-diazonium cation-2', 3-dimethylazobenzene and 2-diazonium cation 4', 5-dimethyl-2'-nitro-3-methoxyazobenzene.

5. The method according to claim 3, wherein the organic solvent is selected from the group consisting of dichloromethane, chloroform methanol, tetrahydrofurn, acetone and nitrobenzine.

6. The method according to claim 3 wherein said salt is 4-benzamido-2,5-diethoxyphenyl diazonium perchlorate.

7. The method according to claim 3 wherein said salt is 4,4'-diazonium perchlorate-3,3'-dimethoxy biphenyl.

8. The method according to claim 3 wherein said salt is 4-benzamido-2,5-diethoxyphenyl diazonium picrate.

9. The method according to claim 3 wherein said salt is 4,4-diazonium picrate-3,3'-dimethoxy biphenyl.

10. A prepackaged stable two-liquid reagent test kit for detecting cannabinoids comprising:
   (a) a substantially stable water-free liquid reagent containing an organic solvent and a diazonium salt which undergoes a characteristic color change when combined with a cannabinoid under basis conditions, said salt comprising a diazonium cation and an anion capable of causing the entire salt including the diazonium cation thereof to dissolve in said organic solvent, and
   (b) a color developing basic solution capable of developing a color in the presence of the water-free liquid reagent and cannabinoids.

11. The test kit according to claim 10 wherein said stable liquid reagent is contained in an aerosol container and dispenser in combination with a propellant selected from the group consisting of compressed air, a fluorohydrocarbon, a chloro-fluorohydrocarbon, $CO_2$ gas, nitrous oxide or $N_2$ gas.

12. The test kit according to claim 10 wherein said basic solution comprises an organic base.

13. The test kit accoridng to claim 12 wherein said organic base is selected from the group consisting of triethanolamine, 4-dimethylaminopyridine, 2-dimethylaminopyridine, 2,4,6-trimethyl-pyridine, piperidine, and 4-(2-piperidinoethyl)pyridine.

14. The test kit according to claim 12 wherein said basic solution is in a sprayable solution containing a solvent selected from a group consisting of ethanol, dichloromethane, chloroform, acetone, methanol and ethylacetate.

15. A stable water-free liquid spray reagent for detecting cannabinoids comprising a propellant in combination with a water-free liquid reagent, wherein said water-free liquid reagent comprises an organic solvent and a diazonium salt which undergoes a characteristic color change when combined with cannabinoids under basic conditions, and wherein said salt comprises a diazonium cation and an anion selected from the group consisting of perchlorate, thiocyanate, trinitrobenzenesulfonate, anthracene-2-sulfonate, picrate, 2,4'-dinitro-α-naphthoxide, salicylate, phenoxymethyl-penicillinate, amobarbiturate, and hexobarbiturate anions, which anion causes the entire salt, including the diazonium cation thereof, to dissolve in the organic solvent.

16. A stable water-free liquid spray reagent for detecting cannabinoids comprising a propellant in combination with a water-free liquid reagent, wherein said water-free liquid reagent comprises an organic solvent and a diazonium salt which undergoes a characteristic color change when combined with cannabinoids under basic conditions, and wherien said salt comprises a diazonium cation and an anion selected from the group consisting of picrate and perchlorate anions, which anion causes the entire salt, including the diazonium cation thereof, to dissolve in the organic solvent.

17. The spray reagent according to claim 16 wherein said diazonium cation is selected from the group consisting of 4-benzamido-2,5-diethoxyphenyl diazonium cation, 4,4'-diazonium cation-3,3'-dimethoxy biphenyl, 1-diazonium cation-2-methoxy-4-nitrobenzene, 4-diazonium cation-2,3-dimethylazobenzene and 2-diazonium cation 4',5-dimethyl-2'-nitro-3-methoxyazobenzene.

18. The spray reagent according to claim 16 wherein said organic solvent is selected from the group consisting of dichloromethane, chloroform, methanol, tetrahydrofuran, acetone and nitrobenzene.

* * * * *